United States Patent
Shao et al.

(10) Patent No.: US 10,121,815 B2
(45) Date of Patent: Nov. 6, 2018

(54) PHOTO DETECTOR AND ASSOCIATED INTEGRATED CIRCUIT

(71) Applicant: Silergy Semiconductor Technology (Hangzhou) LTD, Hangzhou, ZheJiang Province (CN)

(72) Inventors: Lili Shao, Hangzhou (CN); Huisen He, Hangzhou (CN); Baoyu Zhang, Hangzhou (CN); Yanni Zhang, Hangzhou (CN)

(73) Assignee: Silergy Semiconductor Technology (Hangzhou) LTD, Hangzhou (CN)

( * ) Notice: Subject to any disclaimer, the term of this patent is extended or adjusted under 35 U.S.C. 154(b) by 42 days.

(21) Appl. No.: 15/477,032

(22) Filed: Apr. 1, 2017

(65) Prior Publication Data

US 2017/0309670 A1    Oct. 26, 2017

(30) Foreign Application Priority Data

Apr. 21, 2016    (CN) .......................... 2016 1 0259663

(51) Int. Cl.
| | |
|---|---|
| H01J 40/14 | (2006.01) |
| H01L 27/146 | (2006.01) |
| A61B 5/00 | (2006.01) |
| G01J 1/16 | (2006.01) |
| G01J 1/44 | (2006.01) |
| H01L 31/02 | (2006.01) |

(52) U.S. Cl.
CPC ...... *H01L 27/14643* (2013.01); *A61B 5/0044* (2013.01); *G01J 1/16* (2013.01); *G01J 1/44* (2013.01); *H01L 27/14609* (2013.01); *H01L 31/02024* (2013.01)

(58) Field of Classification Search
CPC ......... H01L 27/14609; H01L 27/14643; A61B 5/0044; A61B 5/02427; A61B 5/02444
USPC ............ 250/214 A, 214 R, 214 DC, 214 AL, 250/214 B; 398/202, 208, 210
See application file for complete search history.

(56) References Cited

U.S. PATENT DOCUMENTS

| | | |
|---|---|---|
| 6,987,258 B2 | 1/2006 | Mates |
| 7,244,919 B2 | 7/2007 | Ishikawa et al. |

(Continued)

OTHER PUBLICATIONS

Lingfeng Shi, Design of an Infrared Proximity Sensor with Environment Noise Suppression, Huazhong University of Science and Technology (Natural Science Edition), Feb. 2012, pp. 71-76, vol. 40, No. 2,China.

*Primary Examiner* — Kevin Pyo
(74) *Attorney, Agent, or Firm* — Michael C. Stephens, Jr.

(57) ABSTRACT

A photo detector can include: a light emitting device configured to emit light; a driving circuit configured to drive the light emitting device; a photo-electric conversion circuit configured to generate an optical current signal according to an optical signal; an isolation circuit configured to transmit the optical current signal in an isolated manner; an ambient light filter configured to filter a current component of the optical current signal corresponding to an ambient light, and to generate a clean optical current signal; a current amplification circuit configured to amplify the clean optical current signal, and to generate an amplified optical current signal; (vii) an analog-to-digital converter configured to convert the amplified optical current signal to a digital signal; and a control circuit configured to output an optical detection signal according to the digital signal.

12 Claims, 4 Drawing Sheets

(56) References Cited

U.S. PATENT DOCUMENTS 8,097,840 B2    1/2012   Zheng et al.
9,385,667 B2    7/2016   Lichtenegger et al.
9,775,528 B2 *   10/2017   Vermeulen ............ A61B 5/7203

* cited by examiner

PHOTO DETECTOR AND ASSOCIATED INTEGRATED CIRCUIT

RELATED APPLICATIONS

This application claims the benefit of Chinese Patent Application No. 201610259663.4, filed on Apr. 21, 2016, which is incorporated herein by reference in its entirety.

FIELD OF THE INVENTION

The present invention generally relates to the field of sensors, and more particularly to photo detectors and associated integrated circuits.

BACKGROUND

A photo sensor is a sensor that uses a photo element as a detection element. The photo sensor may initially convert measured changes into optical signal changes, and then convert the optical signal to an electric signal by the photo element. Photo sensors are widely used in heart rate detectors. A heart rate detector can detect a person's heart rate, such that people can determine their own health status based on the detected heart rate. Systole and diastole of the heart causes blood to flow in the blood vessels, and the amount of blood flowing through the blood vessels correspond to different reflectivity. A heart rate detector may calculate the current heart rate by detecting fluctuations of the reflected light.

DETAILED DESCRIPTION

Figure 1:
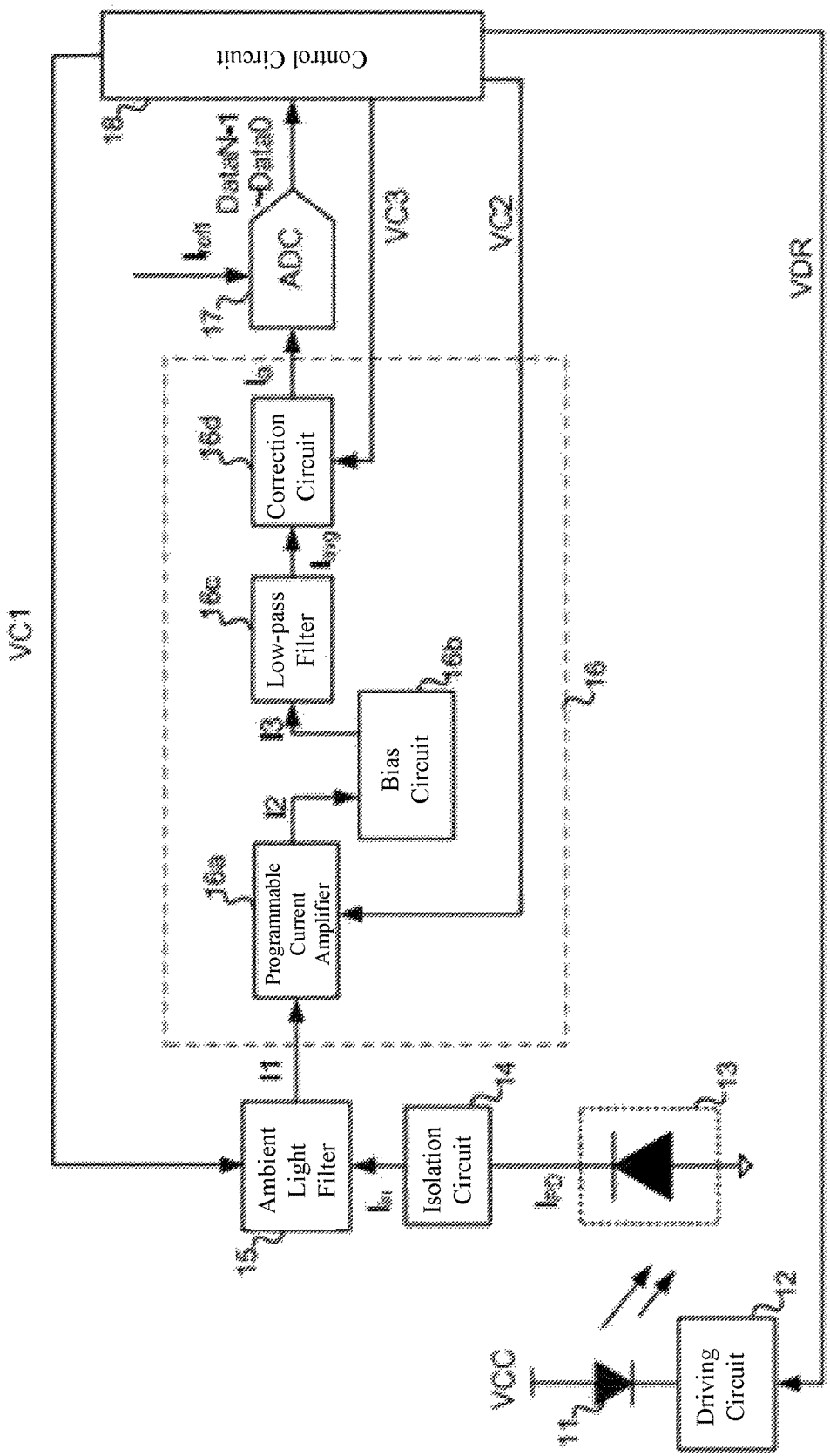
FIG. 1 is a schematic block diagram of a photo detector, in accordance with embodiments of the present invention.

Reference may now be made in detail to particular embodiments of the invention, examples of which are illustrated in the accompanying drawings. While the invention may be described in conjunction with the preferred embodiments, it may be understood that they are not intended to limit the invention to these embodiments. On the contrary, the invention is intended to cover alternatives, modifications and equivalents that may be included within the spirit and scope of the invention as defined by the appended claims. Furthermore, in the following detailed description of the present invention, numerous specific details are set forth in order to provide a thorough understanding of the present invention. However, it may be readily apparent to one skilled in the art that the present invention may be practiced without these specific details. In other instances, well-known methods, procedures, processes, components, structures, and circuits have not been described in detail so as not to unnecessarily obscure aspects of the present invention.

A person may be required to place their fingers or wrists close to a chip when a heart rate sensor is used to detect there heart rate. A light emitting device inside the heart rate sensor chip can emit a detection light, and then the photo-electric conversion circuit can detect the intensity of the detection light that is reflected from the finger or wrist. The photo-electric conversion circuit can generate an optical current by way of illumination, and can convert the optical current to a numerical value through an analog-to-digital conversion circuit. In this way, a person's heart rate may be detected by executing a number of continuous detection actions.

Heart rate sensors are mainly used in portable devices (e.g., bracelets, mobile phones, smart watches, and other electronic products), and such battery powered products may have relatively high power consumption. The power consumption of the light emitting device integrated inside the chip is typically the main power consumption of the heart rate sensor. However, the intensity and light-emitting time of the light-emitting device can directly affect the amplitude of the optical signal that is received by the photo-electric conversion circuit. Resolution of the integral digital-analog converter may directly limit the resolution of subtle changes of the amplitude, and this can affect the output of the sensor. In this case, the light emitted by the light emitting device may be limited to not be too weak, and the time for emitting the light may not be too short. As a result, the power consumption can be relatively large. In particular embodiments, the power consumption can be controlled, and the circuit size may be reduced, of a photo detector suitable for heart rate detection.

In one embodiment, a photo detector can include: (i) a light emitting device configured to emit light; (ii) a driving circuit configured to drive the light emitting device; (iii) a photo-electric conversion circuit configured to generate an optical current signal according to an optical signal; (iv) an isolation circuit configured to transmit the optical current signal in an isolated manner; (v) an ambient light filter configured to filter a current component of the optical current signal corresponding to an ambient light, and to generate a clean optical current signal; (vi) a current amplification circuit configured to amplify the clean optical current signal, and to generate an amplified optical current signal; (vii) an analog-to-digital converter configured to convert the amplified optical current signal to a digital signal; and (viii) a control circuit configured to output an optical detection signal according to the digital signal.

Referring now to FIG. 1, shown is a schematic block diagram of a photo detector, in accordance with embodiments of the present invention. In this particular example, the photo detector can include light emitting device 11, driving circuit 12, photo-electric conversion circuit 13, isolation circuit 14, ambient light filter 15, current amplifier 16, analog-digital converter 17, and control circuit 18. Light emitting device 11 (e.g., an LED) can emit an optical signal, and driving circuit 12 can drive light emitting device 11, in order to emit light. For example, the driving circuit can drive light emitting device 11 in order to emit light pulses according to a pulse sequence generated by control circuit 18 (e.g., light emitting device 11 emits light in a flickering manner). Control circuit 18 can control an output current, duty cycles, and pulse periods, of driving circuit 12 by control signal VDR. Thus, during the measurement, the photo detector can detect the intensity of every light pulse that is reflected by an object in the light pulse sequence, and may obtain an intensity value sequence of the reflected light. In this way, the property of the object, such as heart rate related parameters or changes of distance, can be determined according to the intensity value sequence of reflected light.

Photo-electric conversion circuit 13 can generate an optical current signal according to the optical signal. Those skilled in the art will recognize that photo-electric conversion circuit 13 does not discriminate between the detection light and the ambient light, but may convert all of the received optical signals into an optical current. During a heart rate detection period, the optical current may be at least partially caused by the light generated by light emitting device 11 and reflected by the object. While not in the detection period or when light emitting device 11 is not emitting light, the optical current can actually be caused by the ambient light. For a time period including the detection period, the optical current may partially be caused by the light generated by light emitting device 11. For example, photo-electric conversion circuit 13 may include a photo-diode formed on a semiconductor substrate, such that photo-electric conversion circuit 13 can be integrated with other devices of the apparatus into an integrated circuit chip.

Isolation circuit 14 can be coupled to photo-electric conversion circuit 13, for transmitting optical current signal $I_{PD}$ in an isolated manner. Also, isolation circuit 14 can receive optical current signal $I_{PD}$, and may generate current signal $I_{in}$. For example, current signal $I_{in}$ may be the same as optical current signal $I_{PD}$. Isolation circuit 14 may be implemented by a current mirror circuit, which may not only eliminate effects on the subsequent circuit that may be caused by the photo-electric conversion circuit, but can also change the direction of the current signal, in order to facilitate the setting of the subsequent circuit. Ambient light filter 15 can filter the current component of the optical current signal corresponding to the ambient light and output clean optical current signal I1 (e.g., the optical current caused by the ambient light is filtered). For example, ambient light filter 15 can sample the ambient light of the optical current and filter the current component caused by the ambient light, so as to output the current signal that represents the intensity of the detection light reflected by the object.

In this example, driving circuit 12 can drive light emitting device 11 to emit light pulses by continuous pulse signal sequences (e.g., light emitting device 11 flickers by a predetermined pulse). Thus, the light reflected by the object may flicker along with the light source. All light reflected by the object may represent the property of the detected object at a corresponding time (e.g., the position or color property of the object). Thus, in response to the pulse signal sequence, a sequence in which the object property changes over time during the time period can be obtained, so as to complete the detection.

Ambient light filter 15 can be coupled to driving circuit 12 or control circuit 18 in order to obtain the driving signal sequence of light emitting device 11. Also, ambient light filter 14 can begin ambient light detection before the detection (e.g., before the start of the light pulse sequence). In addition, ambient light filter 14 can detect the ambient light in the gap of light pulses (e.g., the time period during which light emitting device 11 is turned off between continuous time periods during which light emitting device 11 flickers) of the light pulse sequence. Thus, the ambient light can be sampled one or more times during the detection period, without increasing power consumption, so as to improve the accuracy of the photo sensor and the associated photo detector.

For example, ambient light filter 15 can sample the current and obtain the current component that corresponds to the ambient light in a first mode, and also filter the current component corresponding to the ambient light in a second mode. Further, control circuit 18 can switch ambient light filter 15 to the first mode during at least one photo pulse gap of the photo pulse sequence, and may switch the ambient light filter 15 to the second mode when the next optical pulse arrives. Control circuit 18 can switch ambient light filter 15 to the first mode in every photo pulse gap, such that the ambient light can be detected every time after the emitting device emits light during the entire photo pulse sequence, and can also be detected in a corresponding photo pulse gap every few photo pulses. Thus, control circuit 18 may switch the sample and detection circuit to the first mode every predetermined number of photo pulse periods (e.g., every 8 photo pulse periods).

Figure 2:
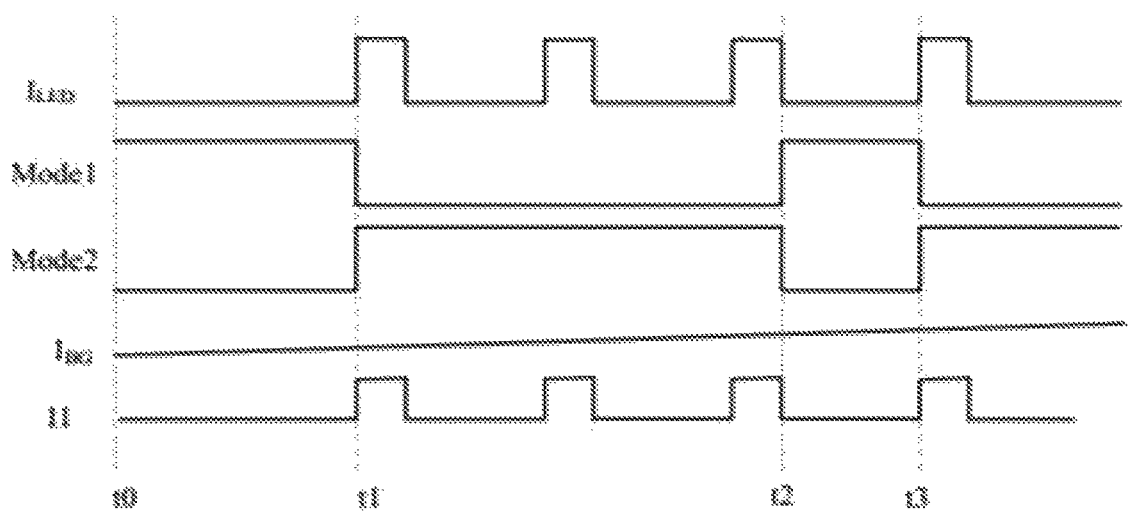
FIG. 2 is a waveform diagram of example operation of an ambient light filter, in accordance with embodiments of the present invention.

Referring now to FIG. 2, shown is a waveform diagram of example operation of an ambient light filter, in accordance with embodiments of the present invention. Photo-electric conversion circuit 13 can receive total current $I_{in}$ caused by light that is a sum of current component $I_{pulse\_current}$ caused by the light pulse signal and current component $I_{BG}$ caused by the ambient light. Current component $I_{pulse\_current}$ may be zero when the light emitting device is not emitting, and current component $I_{BG}$ may dynamically change along with the ambient light. In this example, Mode1 and Mode2 can be complementary timings of mode signals, and $I_{LED}$ may be the driving current of light emitting device 11. From t0 to t1, light emitting device 11 may not be enabled, and only the ambient light is irradiated in photo-electric conversion circuit 13. At this time, ambient light filter 15 can operate in the first mode, and most of the current component $I_{BG}$ caused by the ambient light is substantially the same as optical current $I_{in}$, i.e., $I_{in} \approx I_{BG}$. Thus, current component $I_{BG}$ can be sampled.

From t1 to t2, light emitting device 11 begins operating, the photo pulse signal reflected by the object and the ambient light may be irradiated in photo-electric conversion circuit 13, and ambient light filter 15 can operate in the second mode. Here, the current component corresponding to the ambient light may be filtered from optical current $I_{in}$. In this way, effects of the ambient light can be substantially eliminated without increasing the power consumption of the light emitting device.

From t2 to t3, after a predetermined number of photo pulse periods (e.g., 3), in the photo pulse gap, ambient light filter 15 may operate in the first mode, and the ambient light can again be detected. It can be seen from FIG. 2 that the photo pulse gap during the time interval from t2 to t3 is in the middle of the entire photo pulse sequence, and the photo pulse sequence required in a measurement may not yet be complete. Thus, the ambient light can be detected for several times in the middle of the measurement, in order to ensure the accuracy of ambient light filter. From time t3, the circuit may switch to the second mode in order to repeat the filtering operation, and after a predetermined time interval, the current component that corresponds to the ambient light may be sampled in the photo pulse gap. Then, the process can be repeated.

Ambient light filter 15 can sample the ambient light continuously during the detection period when the light emitting device is not emitting light, in order to track the ambient light in time, and to more accurately filter the ambient light, and to substantially eliminate or minimize effects caused by the ambient light. Current amplification circuit 16 may amplifier clean optical current signal I1 in order to generate optical current signal Ia.

Figure 3:
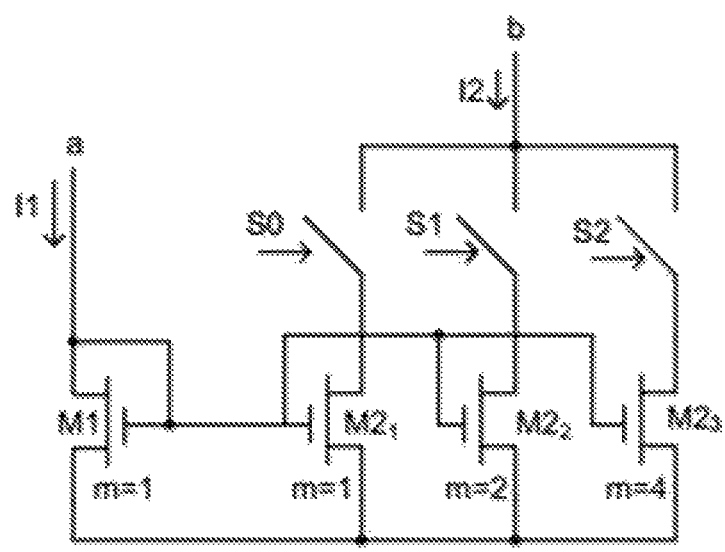
FIG. 3 is a schematic block diagram of a first example programmable current amplifier, in accordance with embodiments of the present invention.
Figure 4:
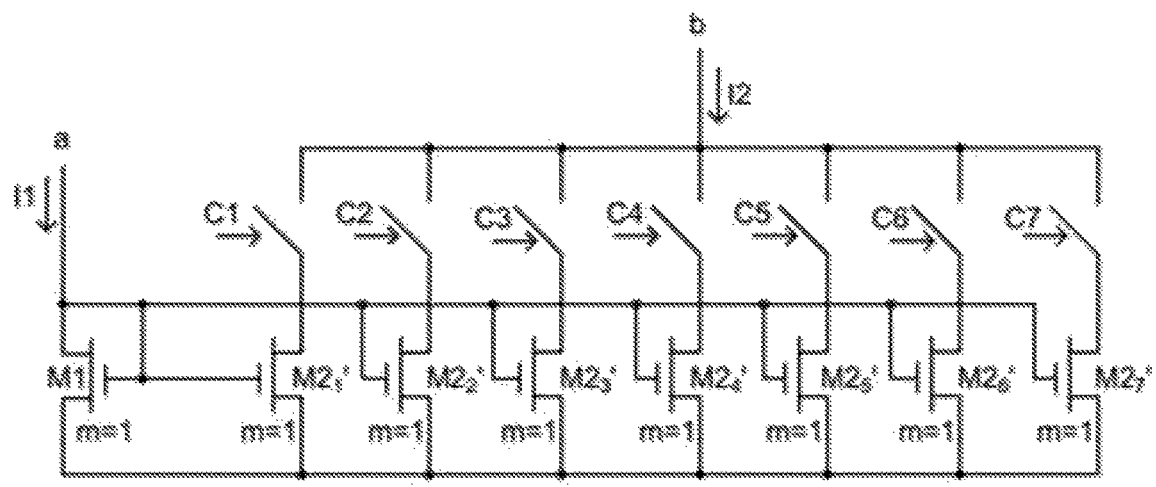
FIG. 4 is a schematic block diagram of a second example programmable current amplifier, in accordance with embodiments of the present invention.

When driving circuit 12 drives light emitting device 11 to emit light in a manner of photo pulses by the photo sequence, filtered optical current I1 provided to current amplification circuit 16 can appear as a pulse sequence or a square wave, in order to facilitate the analog-digital conversion of subsequent analog-digital conversion (ADC) 17. For example, current amplification circuit 16 can include current amplifier 16a, bias circuit 16b, low-pass filter 16c, and correction circuit 16d. Current amplifier 16a can amplifier the optical current signal that is already filtered, and may generate amplification current signal I2. The gain of the current amplifier can be a fixed value or a dynamically adjustable value. For example, current amplifier 16a can be a programmable current amplifier with an adjustable gain. Control circuit 18 can be coupled to the programmable current amplifier in order to output an amplification control signal to control the gain. FIGS. 3 and 4 show different example programmable current amplifiers.

Referring now to FIG. 3, shown is a schematic block diagram of a first example programmable current amplifier, in accordance with embodiments of the present invention. In this particular example, the programmable current amplifier can include transistor M1 and M current amplification branches. The drain and source of transistor M1 can connect between an current input terminal "a" and ground, and gate "g" can connect to the drain. M current amplification branches can be coupled in parallel between current output terminal "b" and ground, where M (e.g., M=3) may be a natural number which is larger than or equal to 2. Each current amplification branch can include transistor $M2_i$ and a corresponding control switch connected in series. The control switch can be controlled by a corresponding control signal Si (i=1~3). The gates of transistors $M2_i$ and transistor M1 can be connected together. Also, the size of transistor M2 in the $i^{th}$ current amplification branch can be ($2^{i-1}$) times the size of transistor M1, i=1, 2 . . . M.

That is, the size of transistor $M2_1$ is the same as that of transistor M1, the size of the transistor $M2_2$ is twice that of transistor M1, and the size of transistor $M2_3$ is four times that of transistor M1. As shown in FIG. 3, "m" can represent the size. Since a transistor's flow capacity is proportional to its size, the flow capacity of the transistor will be stronger when the size is larger. When the control switch in the corresponding branch is turned on, transistors $M2_i$ and M1 may form a current mirror, such that the current flowing through transistor M1 may be replicated or amplified in a corresponding proportion. The current amplification gain of the programmable amplifier can be controlled by controlling the control switch of the current amplification branch.

Referring now to FIG. 4, shown is a schematic block diagram of a second example programmable current amplifier, in accordance with embodiments of the present invention. In this particular example, the current amplification branch of the programmable current amplifier can include transistor $M2'_i$ and a corresponding control switch. The control switch can be controlled by a corresponding control signal Ci (i=1~7). However, all transistor $M2'_i$ may have the same size as transistor M1 in the example of FIG. 4, where "m" can represent the size. When the control switch in the corresponding branch is turned on, transistors $M2'_i$ and M1 may form a current mirror, such that the current flowing through transistor M1 may be replicated in the corresponding branch. A number of parallel coupled current amplification branches can be used in order to amplify the current flowing through transistor M1. The current amplification gain of the programmable amplifier can be controlled by controlling the control switch of the current amplification branch.

For example, control circuit 18 can control the power of driving circuit 12. In a heart rate detection application, the intensities of the optical signals reflected by skins are different due to different human colors. For example, the intensity of the optical signal reflected by white skin AB relatively strong, while the intensity of the optical signal reflected by black skin may be relatively weak, where the optical signal is emitted by light emitting device 11. If the optical pulse signal is weak, the heart rate detection may fail, or the detection result may otherwise not be accurate. In order to ensure the accuracy of the measurement of the heart rate detection system at any time, control circuit 18 can determine whether the optical pulse signal is too weak according to the digital signal. In this case, the driving current of the driving circuit may be increased to increase its power, and the gain of the programmable current amplification may be regulated in order to enlarge the adjustment range, but not to significantly increase the system power consumption.

Bias circuit 16b may add bias current Ib to amplification current signal I2, in order to generate amplification current I3. The function of adding bias current Ib is to increase the amplitude of the current flowing to subsequent low-pass filter 16c, in order to increase the start-up speed at the initial state, and to prevent the current from being too low to affect the performance.

Low-pass filter 16c can generate average current signal $I_{avg}$ according to amplification current signal I3. Low-pass filter 16c may take an average of amplification current signal I3 that appears as a pulse sequence or a square wave, such that the current energy distribution is uniform to facilitate the accuracy of the subsequent analog-to-digital conversion. Correction circuit 16d can filter the bias current from the average current signal to output amplified optical current signal $I_a$. Correction circuit 16d may generate the operation timing of light emitting device 11 from control circuit 18, and can sample when light emitting device 11 is not emitting light, and in such case, the sampled signal is the bias current. When light emitting device 11 is emitting light, correction circuit 16d can filter the sampled bias current from average current signal $I_{avg}$, and thereby substantially adverse effects on the circuit due to the bias current. In this way, amplified optical current signal Ia can be generated.

Analog-to-digital converter 17 can convert the amplified optical current signal to an N-bit digital signal Data0-DataN-1. For example, control circuit 18 can generate a photo detection signal according to the digital signal. Reference current Iref1 used for quantization may be provided by a current reference circuit, and the quantization can be calculated as shown below in Equation (1).

$$DataN = INT\left[\frac{AVG(Ia)}{Iref1} * 2^N\right] \quad (1)$$

In this Equation, INT(*) is a rounding function, and AVG(*) is an average function. The current reference circuit can provide reference voltage $I_{ref2}$ for an oscillator module, and the oscillator module may provide clock signal CLK for a digital signal processing unit. The digital signal processing unit can operate as a chip brain, in order to control the modules to operate at certain timing, and may include a certain number of registers to temporarily store the quantized data.

In a heart rate detection example, a single group of data may essentially be useless, but a plurality of groups of data can be used to calculate the heart rate cycle. Thus, the quantized data can temporarily be stored in the register of control circuit 18. When a predetermined amount of data is stored, groups of data can be transmitted to an external micro-control unit by any suitable data interface (e.g., I2C interface) for subsequent processing. As shown in FIG. 1, control circuit 18 can control ambient light filter 15, programmable amplifier 16a, and correction circuit 16d by respective control signals VC1, VC2 and VC3, such that the corresponding device can process the corresponding current signal according to the driving signal timing of driving circuit 12.

As described herein, light emitting device 11 can be controlled to facilitate optical conversion device 13 to receive the emitted light signal, such that the circuit components other than light emitting device 11 can all be integrated into a single integrated circuit chip. Moreover, certain embodiments can be substantially implemented by transistors, in order to simplify the peripheral circuitry and to reduce the overall circuit size. In this way, external signal interference, and overall manufacturing costs can be reduced as compared to other approaches.

The embodiments were chosen and described in order to best explain the principles of the invention and its practical applications, to thereby enable others skilled in the art to best utilize the invention and various embodiments with modifications as are suited to particular use(s) contemplated. It is intended that the scope of the invention be defined by the claims appended hereto and their equivalents.

What is claimed is:

1. A photo detector, comprising:
   a) a light emitting device configured to emit light;
   b) a driving circuit configured to drive said light emitting device;
   c) a photo-electric conversion circuit configured to generate an optical current signal according to an optical signal;
   d) an isolation circuit configured to transmit said optical current signal in an isolated manner;
   e) an ambient light filter configured to filter a current component of said optical current signal corresponding to an ambient light, and to generate a clean optical current signal;
   f) a current amplification circuit configured to amplify said clean optical current signal, and to generate an amplified optical current signal;
   g) an analog-to-digital converter configured to convert said amplified optical current signal to a digital signal; and
   h) a control circuit configured to output an optical detection signal according to said digital signal.

2. The photo detector of claim 1, wherein said isolation circuit is a current mirror coupled between said photo-electric conversion circuit and said ambient light filter.

3. The photo detector of claim 1, wherein said driving circuit is configured to drive said light emitting device to emit an optical pulse according to a pulse sequence generated by said control circuit.

4. The photo detector of claim 3, wherein said ambient light filter is configured to sample a current and to obtain said current component corresponding to said ambient light in a first mode, and to filter said current component corresponding to said ambient light from said current in a second mode.

5. The photo detector of claim 4, wherein said control circuit switches said ambient light filter to said second mode at the start of an optical pulse sequence, and switches to said first mode in at least one optical pulse gap of said optical pulse sequence, and switches back to said second mode when a next optical pulse arrives.

6. The photo detector of claim 1, wherein said current amplification circuit comprises:
   a) a current amplifier configured to amplifier said clean optical current signal, and to generate a first amplification current signal;
   b) a bias circuit configured to add a bias current to said first amplification current signal, and to generate a second amplification current signal;
   c) a low-pass filter configured to output an average current signal according to said second amplification current signal; and
   d) a correction circuit configured to filter said bias current from said average current signal, and to generate said amplified optical current signal.

7. The photo detector of claim 6, wherein:
   a) said current amplifier comprises a programmable current amplifier; and
   b) said control circuit is configured to regulate an output power of said driving circuit and a gain of said programmable current amplifier according to said digital signal.

8. The photo detector of claim 7, wherein said programmable current amplifier comprises:
   a) a first transistor having a drain and a source coupled between a current input terminal and ground, a gate coupled to said drain;
   b) M current amplification branches coupled a current output terminal and ground, wherein M is a natural number greater than or equal to 2, wherein each said M current amplification branch comprises a second transistor and a control switch coupled in series, wherein gates of said first and second transistors are coupled together.

9. The photo detector of claim 8, wherein a size of said second transistor of an ith current amplification branch is $(2i-1)$ times that of said first transistor, wherein i is a positive integer.

10. The photo detector of claim 8, wherein each of said second transistors has a same size as said first transistor.

11. The photo detector of claim 1, wherein said driving circuit, said photo-electric conversion circuit, said isolation circuit, said ambient light filter, a current amplification device, said analog-to-digital converter, and said control circuit are configured in an integrated circuit.

12. The photo detector of claim 1, configured in a heart rate detector or a distance detector.

* * * * *